United States Patent [19]

Dourdeville et al.

[11] Patent Number: 4,767,279

[45] Date of Patent: Aug. 30, 1988

[54] FLUID COMPOSITION AND VOLUMETRIC DELIVERY CONTROL

[75] Inventors: Theodore A. Dourdeville, Southborough; David L. Trumper, Plainville, both of Mass.

[73] Assignee: Millipore Corporation, Bedford, Mass.

[21] Appl. No.: 57,514

[22] Filed: Jun. 20, 1987

[51] Int. Cl.$^4$ .......................... F04B 49/00; F04B 49/06
[52] U.S. Cl. ........................................ 417/18; 417/22; 417/53; 210/101; 210/198.2
[58] Field of Search ............................ 417/18, 22, 53; 210/101, 198.2

[56] References Cited

U.S. PATENT DOCUMENTS

| | | | |
|---|---|---|---|
| 3,869,067 | 3/1975 | Ashmead et al. | 222/70 |
| 3,917,531 | 11/1975 | Magnussen | 210/101 |
| 4,045,343 | 8/1977 | Achener et al. | 210/101 |
| 4,128,476 | 12/1978 | Rock | 210/31 |
| 4,137,011 | 1/1979 | Rock | 417/22 |
| 4,311,586 | 1/1982 | Baldwin | 210/101 |
| 4,326,837 | 4/1982 | Gilson | 417/22 |
| 4,352,636 | 10/1982 | Patterson | 417/22 |
| 4,427,298 | 1/1984 | Fahy et al. | 366/132 |
| 4,448,692 | 5/1984 | Wakamoto | 210/101 |
| 4,492,524 | 1/1985 | Koch | 210/101 |
| 4,552,513 | 11/1985 | Miller | 417/18 |
| 4,595,496 | 6/1986 | Carson | 210/101 |

OTHER PUBLICATIONS

"A Versatile Gradient Elution Device for HPLC", D. L. Saunders, Journal of Chromatographic Science, vol. 15, Mar./Apr. 1977.

*Primary Examiner*—William L. Freeh
*Attorney, Agent, or Firm*—Hamilton, Brook, Smith & Reynolds

[57] ABSTRACT

An inner short-term pressure sensitive feedback loop is combined with an outer long-term volumetric delivery feedback loop to supply a substantially constant volumetric flow of mixed fluids to a load. The invention has particular utility in the controlled delivery of solvents for liquid chromatography.

27 Claims, 8 Drawing Sheets

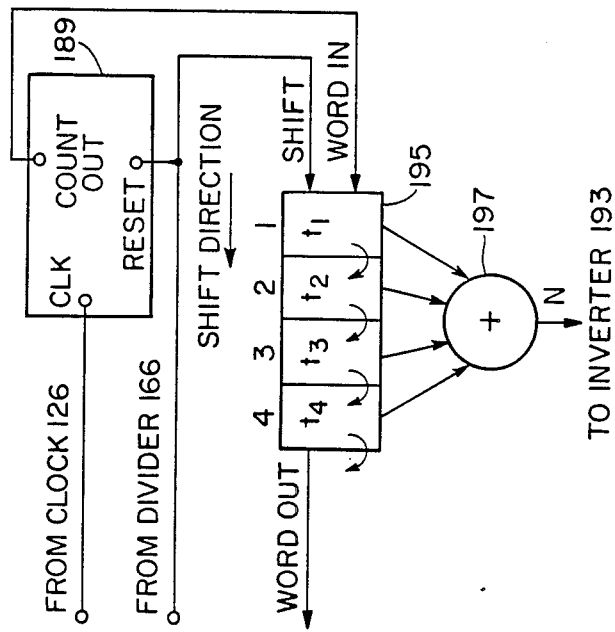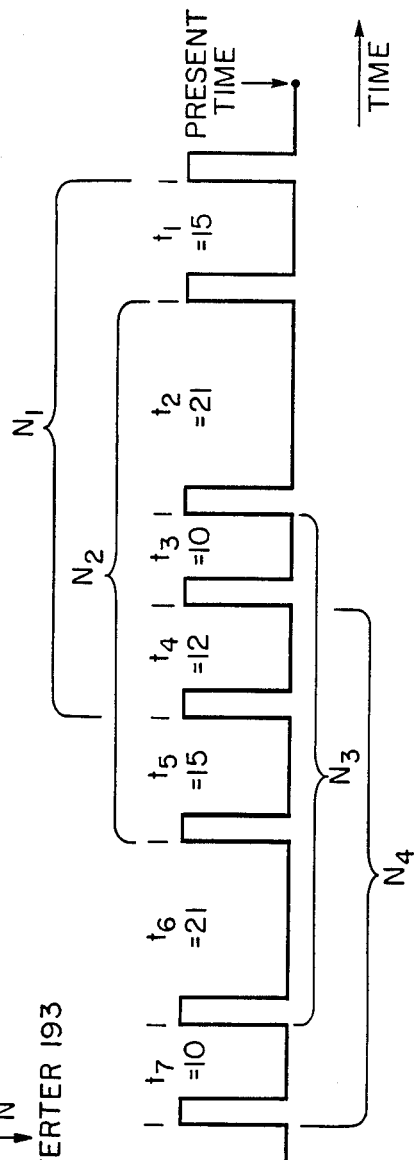
Fig. 3
Fig. 4

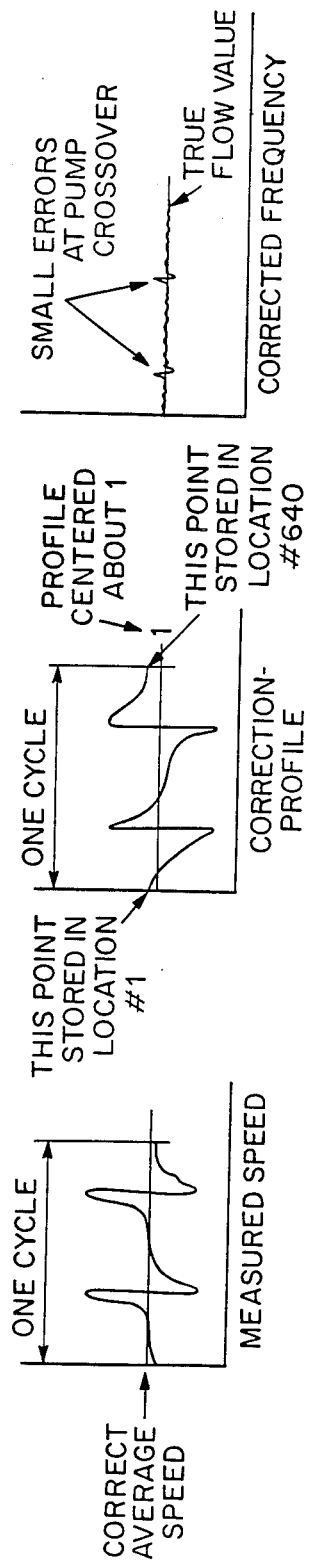

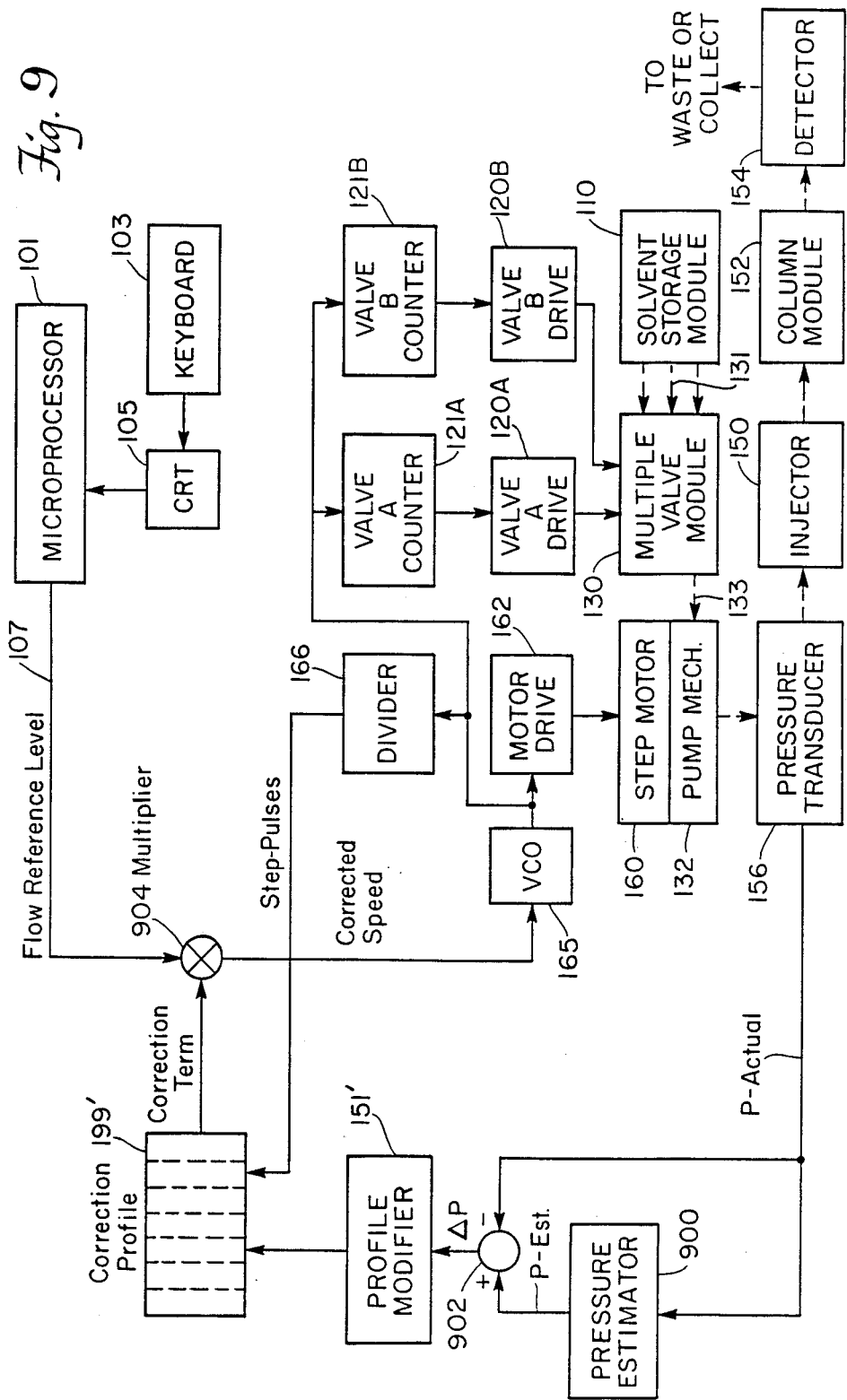

FLUID COMPOSITION AND VOLUMETRIC DELIVERY CONTROLcl DESCRIPTION

1. Technical Field

This invention relates generally to the mixing and delivery of fluids to a load in controlled proportions and volumetric flow. Specifically, the invention relates to the production of a mixture of liquids and the delivery of a controlled flow of this mixture to a point of use. More particularly, the invention pertains to the ability to change the proportions of this mixture with time and to subsequently deliver the desired mixture over a range of flow rates in an accurate, repeatable manner, that is suitable for use in liquid chromatography applications. tions.

2. Background Art

There are many applications which require mixing of fluids and, specifically, liquids in controlled proportions and subsequent delivery of an accurate flow of the mixed fluids. One such application is liquid chromatography wherein a liquid sample is passed by a flowing stream of liquid solvent (the mobile phase) through a column (load) packed with particulate matter (the stationary phase). While passing through the column, the various components in the sample are differentially adsorbed and desorbed from the stationary phase, such that these individual components elute from the column at different times. The separated components then flow through a detector which responds to each component, quantitatively, thereby providing information to the user about the constituents of the sample.

To achieve more effective separations, high performance liquid chromatography (HPLC) systems often use mixtures of solvents as the mobile phase. When this mixture is held constant, the system operates in an isocratic mode, whereas gradient chromatography is achieved when the components of the mixture are changed over time. The present invention has utility for either mode of operation.

Such mixtures of chromatographic solvents can be accomplished by having redundant high pressure pumps with each pump delivering its precise portion of liquid required to a mixing chamber downstream of the pump (i.e., high pressure side). However, these pumps are expensive, and the overall cost and complexity of the system is undesirably increased.

Alternatives have been proposed in the past to perform the desired metering at the low pressure side of the pump. Most often, such systems include a plurality of reservoirs containing the liquids to be mixed, with each reservoir being suitably connected to the inlet of the pump. A valve arrangement between the reservoirs and the pump inlet, meters each liquid in predetermined proportions.

To meter the solvent volumes, the individual valves are sequentially actuated during the pump draw stroke. However, the amount of liquid taken in per unit of time of valve actuation varies and the piston velocity varies throughout the stroke. These variables can create significant errors in the compositional mixture and volume delivered per unit time. Some of these errors vary over time and produce a compositional error that is detected as a "ripple" which interferes with the ability to detect and quantitate chromatographic peaks.

A substantial amount of research and development has occurred, over many years, in an attempt to solve or minimize the aforementioned problems. A number of patents have issued suggesting various averaging, open loop compensating, and feedback metering techniques. For example, U.S. Pat. No. 3,869,067 shows an averaging technique, U.S. Pat. No. 4,045,343 discloses an open loop compensating technique and U.S. Pat. No. 4,128,476, a feedback error signal technique.

Other attempts to minimize the interaction between valve cycles and pump cycles in a liquid chromatography multiple solvent delivering system are found in U.S. Pat. No. 4,427,298 and in an article by D. L. Saunders entitled "A Versatile Gradient Elution Device for HPLC" (*Journal of Chromatographic Science*, Vol. 15, March/April 1977).

More recently, in U.S. Pat. No. 4,595,496, a method and apparatus for generating extremely smooth, multisolvent compositions is disclosed. In this system, the valve "On" duration is established by accumulating pulses which correspond and are identical to the pump stepping motor drive pulses. The phase relationship between valve proportioning cycles and piston intake cycles is constantly shifted in accordance with a fixed relationship established between switching valve cycles and pump cycles. This relationship is governed by the ratio of the pump cycle time over the switching valve cycle time, optimally expressed as a non-integer ratio. In this manner, the non-uniformity associated with the pump draw stroke is effectively averaged over several cycles of switching valve actuations.

While the system of U. S. Pat. No. 4,595,496 has proven successful in substantially eliminating the compositional ripple effect caused by transient pump behavior, it does not address, nor does it solve, problems associated with accurate and repeatable delivery of a desired volume per unit time of a desired compositional mixture.

Undesired variations in chromatographic flow rate occur as a result of variation in solvent compressibility and the associated variabilities of the compliance of pump materials and prevailing chromatographic back pressure. This problem is exacerbated in gradient chromatography wherein the solvents in the mixture are changing with time. As a result, there is no single practical satisfactory mechanical solution to this problem. Instead, dynamically variable feedback-controlled electromechanical solutions have been proposed.

Because of its superficial resemblance to the present invention, one such prior art solution will be discussed in detail below, in connection with the PRIOR ART drawing of FIG. 1. The apparatus shown in FIG. 1, herein, is taken from FIG. 1 of Pat. No. 4,137,011 issued Jan. 3, 1979 to John V. Rock. This system will hereafter be referred to as the Rock system.

In the Rock system, solvent storage module 10 contains storage containers for the liquid components, i.e., solvents used to make up the carrier or mobile phase of the liquid chromatography (LC) system. The storage containers or units provide a source of liquid(s) to a pump module 30 at atmospheric or low pressure. The individual storage units are connected through suitable piping 31 to a composition control module 20 containing digitally controlled valves which are programmed during the intake strokes to select, over predetermined time intervals, liquids from each of the storage units and pass the liquids through a common mixing channel to the flow control pump module 30. The pump module 30 generally includes a single positive displacement pump having opposed pump chambers containing pistons within the cylinders driven by and in conformance with the shape of a cam. The liquid output of the pump is coupled for separation to an injection module 50 at the head of a liquid chromatography (LC) column module 52. The output of the LC column is detected in known manner by a detection module 54 using light transmission or other detection techniques.

At the inlet end of the LC column 52 and injection module 50, a flow-through pressure transducer 56 is located. The voltage output signal of the pressure transducer to switch 68 forms one basis for the inner pressure feedback loop of the flow control circuit of the Rock system.

A pump in pump module 30 is driven by stepping motor 60, which in turn, is driven by step-pulses derived from step generator 62. The frequency of the pulses and, hence, the speed of the stepping motor, can be changed by flow rate controller 63 when coupled through switch 22.

The step generator 62 also responds to the output of a differential amplifier or comparator circuit 64. Amplifier 64 generates a voltage error signal, $\Delta P$, which is converted through a voltage-to-frequency converter 65, into a series of frequency pulses to speed-up or slow-down step generator 62. The error signal results from comparing, in comparator 64, the measured value (P-ACTUAL) of the back pressure from pressure transducer 56 with a predetermined pressure reference level (P-REF) supplied by a RAM module 66. Comparator 64, voltage-to-frequency converter 65, pump driver 62, stepping motor 60, and pressure transducer 56, form an "inner" pressure feedback loop whenever switch 68 is closed to connect the voltage output of transducer 56 to one input side of comparator 64.

The Rock system is exercised through three distinct modes of operation (termed Phases I, II, and III) to obtain stabilized flow output.

In Phase I, switch 22 connects flow rate controller 63 to generator 62. This causes the stepping motor 60 and the pump in pump module 30 to operate at fixed rotating and reciprocating rates, respectively, selected by the user and set by controller 63. These rates are the approximately correct average rates required to generate a solvent flow rate equal to the desired value required by the user. This causes a chromatographic system pressure to be generated, which is typical of system operation for that specified set of conditions (i.e., column geometry, solvent composition, temperature, etc.). This system pressure is sensed by the pressure transducer 56, the output of which is captured in switch position I of switch 68 during a prescribed interval and encoded, and recorded in memory (RAM 66). While the pressure transducer output, as a function of time, will include all the transient fluctuations encountered during piston crossover, only a single set of values is stored at this time in Phase I.

In Phase II, switch 68 is closed to deliver the output of pressure transducer 56 to one side of amplifier 64 and switch 70 is closed to deliver the pump driver signal to the motor speed reference memory (RAM) 72. The operation of the system is continued, the pressure reference memory RAM 66 continues supplying a demand pressure, which is followed by changes in the pump driver speed caused by any fluctuations appearing in the pressure output.

Thus, in Phase II, the pressure is held constant at the demand level, while the motor speed is allowed to vary to develop a motor drive speed pattern in RAM 22, which compensates for otherwise existing pulsations in output pressure and flow. Multiple switch actuations of switches 68, 22 and 70 decouple the pump electronic drive from the controller 63 and, instead, drive the pump in a pressure-feedback servo mode, utilizing as the pressure reference set-point, the value which was stored in memory 66 during Phase I.

This "inner" feedback loop compares the pressure reference value, from RAM 66, with the actual system pressure being sensed by the transducer 56, and generates an error signal, $\Delta P$, the value of which is a function of the magnitude and sign of the difference detected between the two inputs to amplifier 64. This error signal is used to drive voltage-to-frequency converter 65, the output of which is applied to the pump driver 62. The sense of the system is such that detected system pressure, which is less than the reference pressure, will cause an increase in the frequency output of the voltage-to-frequency converter, increasing the pump reciprocating rate, and thereby increasing system pressure by increasing the flow rate. Phase II operation is thus capable of holding pressure very constant, by modulating the stepping motor/pump speed. The modulation pattern required to vary motor speed to keep pressure constant is characteristic of the system for that specified set of conditions. This pattern of variation is encoded and stored in RAM 72.

An LED-optical interrupt device 74 is triggered by an indexing mechanism on the pump cam in pump module 30. Device 74 generates a start pulse to clock 76 as a starting point, or reference position, for collecting and storing the speed pattern in RAM 72 and indicates each time interval of operation of a complete pump cycle for synchronizing the system operation.

In the operational phase (Phase III), switch 70 connects a portion of the signal from pump driver 62 to counter 88 while switch 68 continues to maintain the inner loop connected and in operation through amplifier 64. An interval "n", which is shorter than one complete revolution, is selected and the stored speed pattern values are delivered from memory 72 to count-to-voltage converter 86 and one input of differential amplifier 80. The pump driver 62 operates during the interval "n" causing counter 88 to sum up the total number of step-pulses received. At the end of the interval "n", gate 90 opens to deliver the number for that interval to count-to-voltage converter 92 and one input of the differential amplifier 80, the output of which passes through gate 84 as a correction to the pressure reference signal P-REF for the next successive interval "n".

The next pulse arrives and resets the gates. In this way, the actual count of step-pulses of each interval of the driving step function is compared in differential amplifier 80 with the stored value for that interval "n". At the end of each interval "n", a change in demand pressure is computed and used for the next successive interval.

In the Rock system, by reiterating this process in each interval, the demand pressure supplied by the pressure reference P-REF from RAM 66 is varying so as to eliminate pulsations in the output while permitting an overall gradual change in output pressure to accommodate changes in system operating variables, such as viscosity, which would otherwise affect the ability of the pump to deliver constant flow.

The premise underlying the Rock system, is that while motor step counts in adjacent intervals "n" are highly non-uniform (due to corrections applied by the pressure feedback loop), counts derived from the "equivalent" or corresponding intervals (from one complete pump revolution to the next) should be reproducible if the flow rate is correct. If the number of motor steps actually accomplished in a specific interval is low with respect to the value stored in RAM 72 then the motor 60 is running too slowly, and the pressure reference from RAM 66 for the inner feedback loop should be set higher by an amount which is proportional to the error sensed in that interval.

The Rock system's reliance on a memorized calibration cycle results in an inherent disadvantage and several serious shortcomings. The characteristic variations in motor speed required to maintain pressure constant is obtained from a calibration run performed in a constant pressure mode and is recorded in RAM 72. However, those variations are characteristic only for that single specified set of conditions. In the course of a gradient run, changes in solvent composition and temperature result in very significant changes in both the hydraulic resistance (hence the prevailing back pressure) and the solvent compressibility.

The pattern of motor speed variation, which is required to produce uniform flow at one set of conditions, is very different from that required at another point in the gradient run. Locking the correction loop into a single, highly specified pattern of response, is an untenable method for dealing with dynamically changing system properties. Additionally, this technique assumes that, even under a specified set of conditions, one can truly acquire a single representative motor speed variation pattern.

The Rock system approach recognizes that left and right piston deliveries are typically mismatched, and for this reason, records through an entire pump revolution, not relying on an argument of symmetry. However, while the gross aspects of fluid delivery are reasonably repeatable from one revolution to the next (under fixed chromatographic conditions), the details or "fine structure" of the correction cannot be assumed to be identical. Check valve and seal behavior are not ideal, and produce departures from expected motor velocity patterns. The use of a single stored speed pattern in RAM 72 does not accommodate this departure from calibrated conditions.

The interval-by-interval comparison technique employed in the Rock system for closing the outer loop imposes additional limitations on the system performance. In the Rock system, one complete pump revolution is divided into a number of smaller intervals. This is advantageous in order to decrease the time required to respond to a real flow rate error, and to decrease the magnitude of the discrete correction (flow rate change) applied. But, legitimate comparisons between "called-for" and "delivered" flow can only be made when similar regions of the motor velocity curve are being compared.

The advantage of shortening the duration of a sampling interval is to increase the frequency of the flow corrections. This reduces the amplitude of the correction applied in any one interval. In turn, discontinuity is minimized, making the system response more nearly continuous and smooth. However, this advantage cannot be fully realized in practice, because of the increasing effect of count noise and calculation error, as the interval duration shrinks.

In the Rock system, the cam position indexing reference provided by the LED/optical interrupt 74, is used to ensure that the sampled regions of the velocity profile stored in memory can be correctly compared to the corresponding regions sampled in actual feedback-controlled operation. The actual chromatographic conditions of, for example, solvent composition and temperature, change in a smooth and continuous fashion. But, the control technique of the Rock system; which uses ratios of observed versus expected motor steps per interval, produces, in principle, a discontinuous series of step changes of flow rate in response.

In a discretely sampled digital system, such as the Rock system, there is a minimum inherent uncertainty of plus or minus one count in the quantization of motor rotation in a given interval. Added to this is noise in the measurement from other sources. For example, the non-ideal behavior of check valves cause the fine structure of the motor speed modulation pattern to be slightly different from stroke-to-stroke. When the total number of counts sampled in an interval is very high (e.g., one thousand or more, corresponding to a significant fraction of a full pump revolution), the contribution of these sources to inaccuracy in the measurement is relatively small. As the duration of the interval is reduced (e.g., by a factor of ten or a hundred), the effect of this noise on the measurement is magnified.

In addition, as the magnitudes of the two numbers which are being used to generate the flow rate ratio, i.e., the "called for" versus "delivered" ratio diminish, the coarseness of the correction increment increases. Thus, the increment of plus or minus 1 part in N parts, or 1/N, is large for small values of N, but decreases as N increases, approaching zero as N approaches infinity. The capability to discern small changes in flow rate and to respond correctly without overshoot, is lost as the interval becomes small, as required in the Rock system.

The above detailed analysis of the known state-of-the-art in the control of chromatographic flow rate and solvent mixture, indicates that despite the expenditure of considerable time and money and creative resources in this area, a need still exists for an improved control system for providing smooth and accurate solvent compositional delivery with minimal pulsile variations in volumetric delivery. This system should not depend on the generation of a reference calibration run and should not rely on relatively wide discrete sampling intervals for either gradient generation or flow control.

DISCLOSURE OF THE INVENTION

In the apparatus of the present invention, an inner short-term pressure sensitive feedback loop is combined with an outer long-term volumetric delivery feedback loop for essentially constant volumetric delivery of fluid to a load, despite cyclic variations in relation between motor speed and pump flow. The apparatus is capable of adjusting to changing pump operating conditions throughout the course of pump operation. Typically, the apparatus is utilized in a liquid chromatography (LC) system. The LC system includes a source of liquids coupled through valves to a cyclical pump for delivery of mobile phase liquid solvents to an LC column.

The inner loop comprises a pressure transducer for sampling and generating a signal proportional to the sensed instantaneous actual back pressure at the LC column; and apparatus for determining the extent to which the actual pressure deviates from a reference pressure level or pressure set point (P-SET) established by the outer feedback loop.

To the extent a difference exists, an error signal ΔP is generated, and the pump is either speeded up or slowed down, in accordance with the magnitude and sign of the error signal. The ΔP error signal is amplified and compensated in a gain and compensation feedback circuit and used to drive a voltage controlled oscillator (VCO). The frequency of the VCO controls the frequency of motor-pulses used to drive a motor coupled to the pump. The term "motor-pulse" is intended to indicate any pulse applied to a motor to index the motor by a predetermined increment of motion. Since the frequency of the VCO is directly related to the frequency of the motor-pulses, the motor speed is likewise directly related to the VCO frequency.

The pump and motor are calibrated such that the number of step-pulses "n" required to complete one cycle of the pump is a fixed known entity. The step-pulses may be any sequence of pulses produced at a multiple or submultiple of the motor pulse sequence frequency.

A pump cycle is defined to be one complete sequence of operations from one position of the pump mechanics, until the pump mechanics returns to an identical mechanical position or configuration. That is, starting at an initial mechanical state, and advancing the motor, the pumping mechanics is driver through its various states of operation, and returns to the initial state in one pump cycle. The time (N) it takes to complete one pump cycle is therefore directly proportional to, and can be determined from the time it takes to generate "n" step-pulses; or multiples, or submultiples thereof. The inverse of N is the frequency F or cycles/time. The motor and pump are calibrated such that the volume V of liquid delivered by the pump in one cycle is known. Therefore, the frequency F can be converted to a flow rate using the relationship:

Pump Volume displaced per cycle × F
(number of cycles per unit time) =
Volume delivered per unit time (Flow).

This property is used in the embodiments of the outer loop to establish volumetric flow control.

In a first embodiment, the outer loop comprises a clock pulse generator for generating a series of accurate timing pulses, preferably at a frequency higher than the step-pulse frequency. These timing pulses are successively counted to determine the time duration from one step-pulse to the next step-pulse. The time duration of the n-most recent step-pulses are successively used to determine the time N it takes to complete one pump cycle. This time signal N is inverted to obtain a frequency signal "F" equal to the pump frequency in cycles per unit time. This process is repeated successively, so that N is re-calculated once each step-pulse. Thus, the computed frequency F is the average frequency over each most recent pump cycle.

The signal F is subtracted from a desired flow set point signal F-SET established by the system user. The difference between the two signals (F)−(F-SET)=ΔF is an error signal which, after suitable gain and compensation, is used to set the pressure reference level signal P-SET for the inner loop.

Successive calculation of the time N to complete one pump cycle can be determined in hardware by accumulating clock pulses in a counter circuit for the duration of the time between successive step-pulses, and shifting the count into an n-stage shift register. The sum of the counts in each stage of the register is computed and used to successively determine N. This determination is made for each step-pulse, such that for each complete pump cycle, the number N of clock pulses generated is measured "n" times and averaged over a complete cycle.

Alternatively, the computation can be made in software. A microprocessor, with n-word RAM circular memory locations 1 through n, stores a binary digit word corresponding to the count of timing clock pulses between each step-pulse, for the "n" most recent step-pulses. The time in clock pulses between successive step-pulses is referred to as the step-time. Therefore, the sum of the contents of the n-locations is the time N for one revolution. Initially, memory locations are set to ZERO and the current memory position is set to ONE. After each motor step-pulse occurs, the number of clock pulses previously stored in the current location are subtracted from the previously calculated N. Next, the present step-time counter value is read and stored in the current location and added to N, so that N is now updated. The step-time counter, is then reset and the current memory location set to the next memory position to be ready for the occurrence of the next step-pulse. In this manner, N is updated once each step-pulse.

Optionally, the volumetric control system of the invention may be synergistically combined with the liquid composition control system of the above-referenced U.S. Pat. No. 4,595,496. This is eminently practical because the apparatus of the '496 patent employs composition valve proportioning cycles, the duration of which is specified in terms of a number of pump motor pulses. The undivided set of pulses from the VCO used to drive the pump step motor are accumulated by valve counters or timers which gate the duration of gradient generating drive valves controlling the solvent mix. The "On" duration of a valve is then proportional to the number of motor-pulses and not to any particular time base. Thus, motor speed can be varied, in accordance with the present system, to accommodate flow variations by varying the pulse rate common to both the valve driver and stepping motor, without affecting the mixture of composition delivered.

In an alternate embodiment of the outer loop a microprocessor circular RAM memory having n address locations is used to store a speed/frequency correction value, or factor, as a digital number in each n location; wherein n is the number of step-pulses per pump cycle. The speed correction term for each n steps forms a "correction profile" of the frequency at each n steps over one cycle. The speed correction factor for each n current motor position is multiplied by the measured speed determined in accordance with the outer loop embodiment, described above. The product is the corrected speed F-CORR. Assuming that the "correction profile" is accurate, the corrected speed will be proportional to the true volumetric flow, irrespective of speed modulations which occur on a cyclical basis as a natural result of using the inner pressure loop.

The corrected frequency is subtracted from the setpoint frequency F-SET to produce F, which after suitable gain and compensation, is used to adjust the pressure set point for the inner loop.

The above, and other features and advantages of the invention, will now be explained in detail in connection with the drawings.

BRIEF DESCRIPTION OF THE DRAWINGS

FIG. 3 is a block diagram of a hardware version of the time/cycle circuit 191 of FIG. 2.

FIG. 4 is a timing diagram illustrating the process occurring in FIG. 3.

FIGS. 8A–8C are timing diagrams, respectively, of typical measured speed signals, correcting profile signals and corrected frequency signals generated in the operation of the FIG. 6 embodiment.

FIG. 9 is a block diagram of a further alternate embodiment of the invention, which eliminates the need for direct pressure or flow feedback loops.

BEST MODE OF CARRYING OUT THE INVENTION

Figure 1:
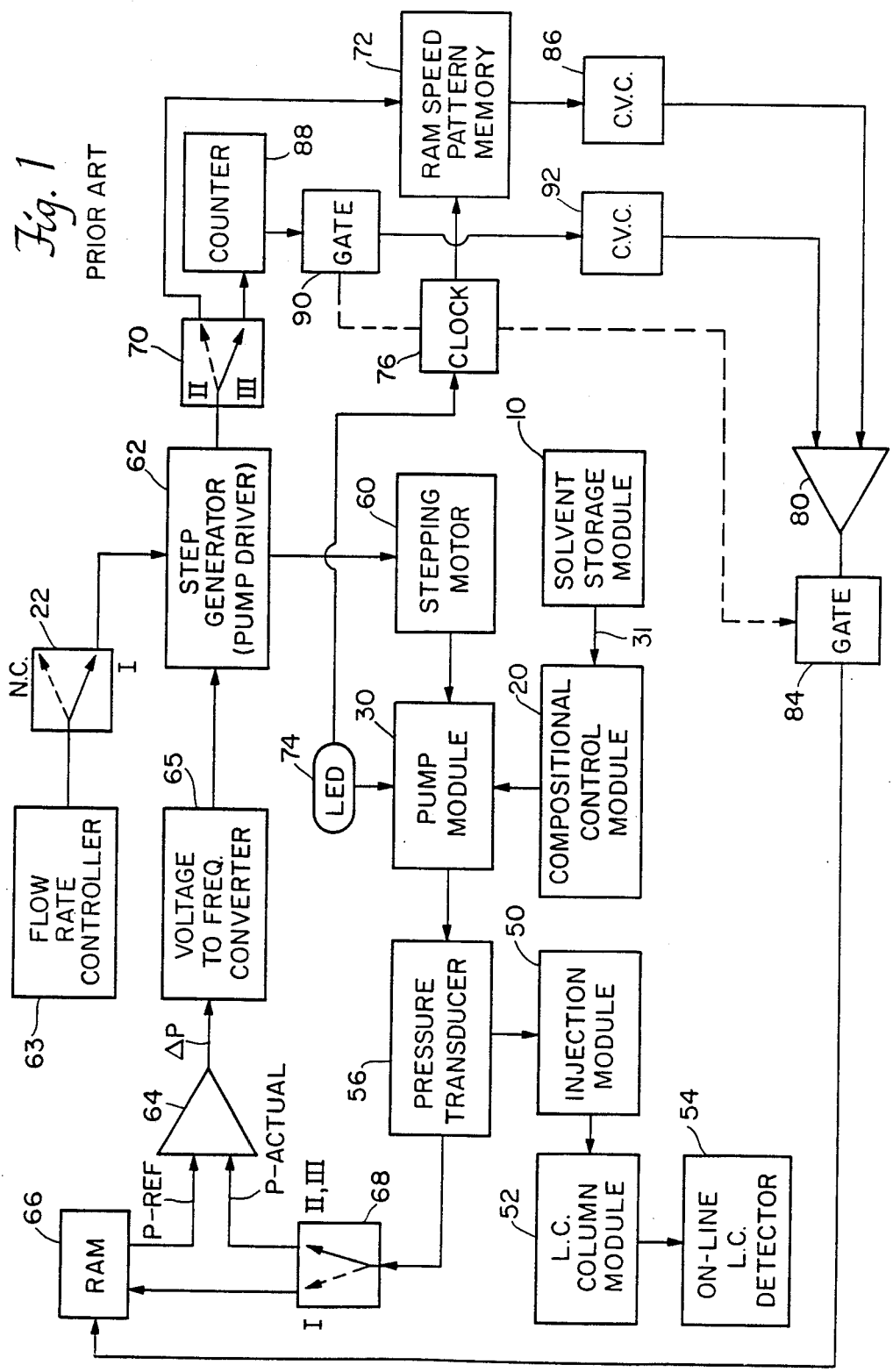
FIG. 1 is a block diagram of the prior art Rock system of U.S. Pat. No. 4,137,011.
Figure 2:
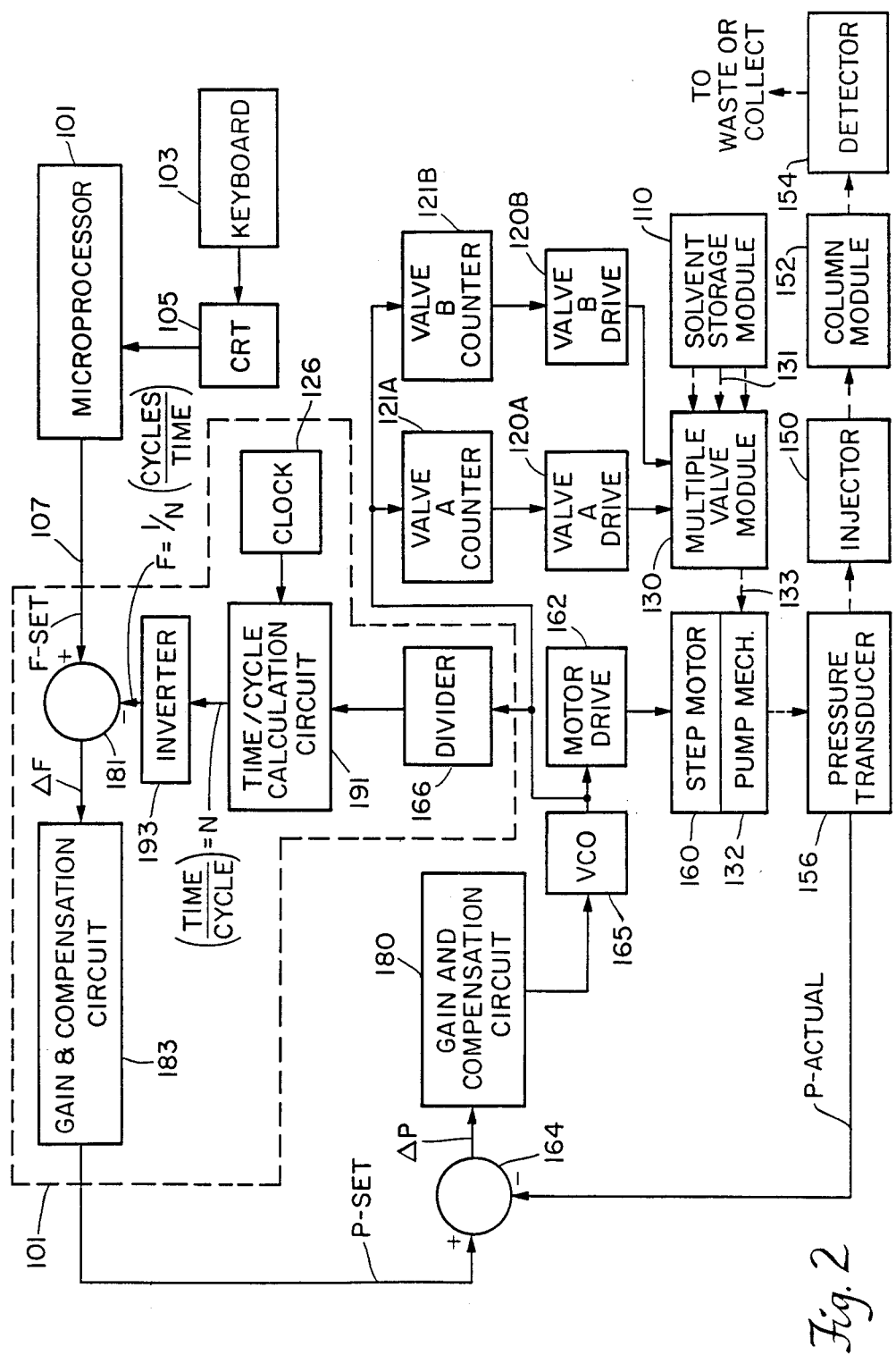
FIG. 2 is a block diagram of the system of the present invention.

Referring now to FIG. 2, the liquid chromatographic system of the invention will now be described, in detail, in connection therewith. Note that hydraulic connections are shown in dotted lines and electrical connections in solid lines.

The motor and hydraulic section of the liquid chromatography system comprises a solvent storage module 110, containing a plurality of liquids in separate containers (not shown). The liquids are coupled by lines 131 to multiple valve module 130, and proportioned by valves driven by valve drivers 120A, 120B, etc. and pumped by a pair of pistons (not shown) in pump mechanics 132, for delivery through pressure transducer 156 to injector 150. One revolution of a crankshaft (not shown) in pump mechanics 132 which drives the pistons constitutes one "pump cycle".

Valve module 130 may comprise a pair of conventional fluid switching valves (not shown) having a common fluid output 133 connected to the inlet port of pump mechanics 132 through check valves (not shown). The fluid outlet port of pump mechanics 132 is coupled through check valves (not shown) to deliver the resultant pumped mixture to the aforesaid injector 150, for delivery to LC column module 152 for inspection by an "on-line" chromatographic detector 154. Valve drivers 120A and 120B are controlled by counters 121A and 121B, respectively. Counters 121A and 121B count the number of motor pulses from voltage control oscillator (VCO) 165 before division by fixed divider 166. These counts are used to establish the ON and OFF times of the respective valve drive circuits.

The composition of the liquid mixture, delivered to the column 152, depends on the relative duration each of the individual valves in module 130 is opened to admit liquid from a particular reservoir within solvent storage module 110. That duration is established in terms of the fraction of a pump cycle accomplished. Note that this duration is not a "time" determined parameter. In other words, valve actuation is locked to motor steps and not to "time". The total elapsed duration for the valve cycle to repeat, which is made up of the actuation and delay duration of the valves, is the proportioning cycle duration.

I. INNER (PRESSURE FEEDBACK) LOOP

Assuming flow has been initiated in the system, such flow causes back pressure to be generated from the injector/LC column 150/152. This pressure is sensed by pressure transducer 156. This system operating pressure, represented as an output voltage P-ACTUAL from the transducer 156, is sampled and provided as the negative input to a summing junction 164. The positive input terminal to summing junction 164 is provided with a pressure reference voltage (P-SET), the value of which is established by the outer control loop, shown within dotted lines 101.

Deviations of sensed pressure (P-ACTUAL) from the reference voltage level P-SET, generate voltage error signal $\Delta P$, which is suitably adjusted in gain and compensated in frequency response in circuit 180, to achieve stable dynamic performance, in accordance with well-known feedback techniques. After gain and compensation $\Delta P$ is converted in VCO 165 to an oscillating signal, the frequency of which is proportional to the difference between the actual and desired pressure. The VCO signal is coupled to motor drive 162 to drive step motor 160; and is reduced in frequency by fixed divider 166 and coupled to time/cycle calculation circuit 191 in outer loop 101. Motor drive circuit 162 converts the pulse train from VCO 165 into a staircase waveform and generates the necessary current therefrom to speed up or slow down stepping motor 160, in accordance with the sense and magnitude of the error voltage $\Delta P$.

The resulting modulation of the speed of pump 132 serves to restore flow to a level which keeps the sensed pressure, P-ACTUAL, equal to the reference pressure, P-SET. The pressure transducer 156, summing junction 164, circuit 180, and VCO 165 form an inner pressure feed-back loop nested within outer flow control loop 101.

Outer loop 101 modulates the reference pressure signal P-SET, in accordance with the sensed deviations $\Delta F$ of actual volumetric flow rate F versus desired volumetric flow rate F-SET. The actual volumetric flow rate is determined by circuitry in the outer loop which counts the number of clock pulses from clock 126 required to complete one cycle.

II. OUTER FEEDBACK LOOP

The circuitry and operation of the outer loop 101 for establishing $\Delta F$ will now be described, in detail. Assume, for example, that the number of motor-pulses, i.e., output pulses from VCO 165, required to drive the pump 132 one complete cycle is fixed and known, e.g., 2560. Assume, also, that these 2560 step-pulses are divided in divider 166 by an integer submultiple number x, such as 640, so that for illustration purposes, 2560 divided by 640=4 step-pulses out of divider 166, each representing one 4th of a cycle of pump 132. Thus, in this example, the number of step-pulses "n" per pump cycle, is n=4.

These divided pulses are coupled to a time/cycle calculation circuit 191, wherein the time N for the recurrence of the most recent n step-pulses, comprising a full cycle, is calculated for each step-pulse. This time N=time/cycle is inverted in inverter 193 to produce F=1/N =cycles/time averaged over the most recent cycle. F is directly related to the actual delivered volumetric flow by virtue of a constant conversion factor related to the swept volume of the pump. F is coupled to the negative input terminal of summing junction 181, where it is subtracted from F-SET on line 107; the cycle frequency set point from microprocessor 101. F-SET is programmed by a system user operating keyboard 103 coupled to CRT 105 and microprocessor 101. The difference signal ΔF between F-SET and F produced by summing junction 181 is adjusted in gain, and frequency compensated, in a conventional feedback circuit 183 and is used to vary the pressure reference set point P-SET. F is recalculated at each step-pulse; therefore, P-SET is successively adjusted, in accordance with the sense and magnitude of F, each such interval.

III. TIME/CYCLE CALCULATION CIRCUIT 191

Figure 5:
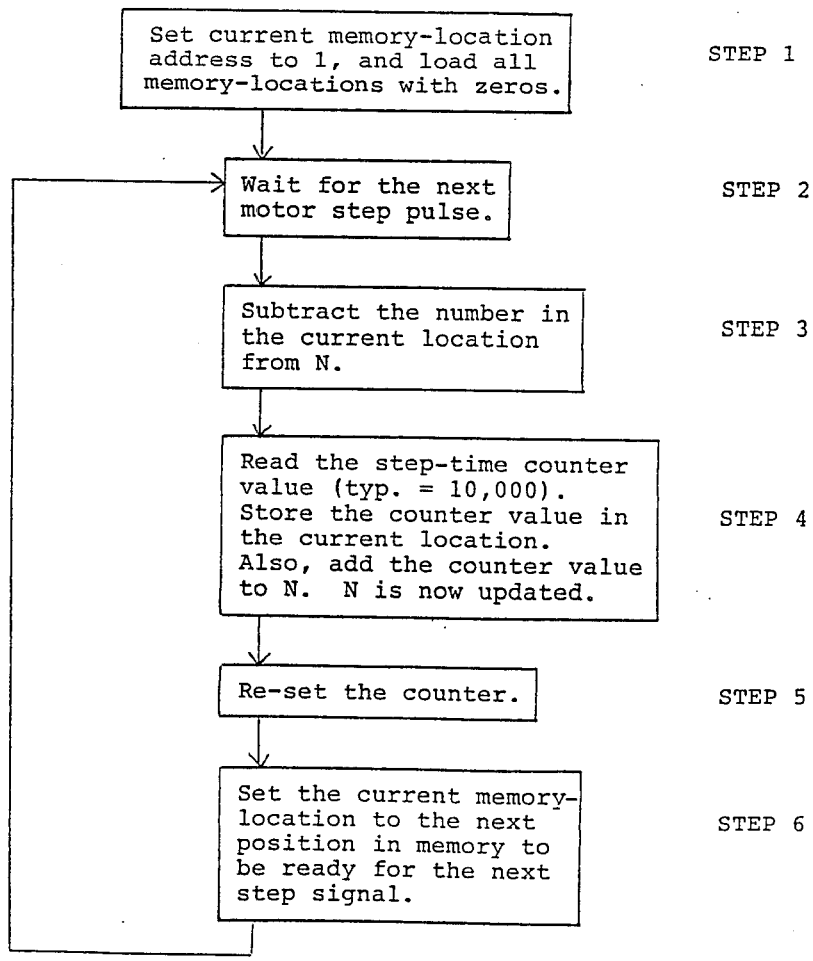
FIG. 5 is a flow chart of a software version of the circuit of FIG. 3.

Suitable apparatus for producing the time/cycle calculation will now be described in connection with FIGS. 3, 4 and 5.

IV. HARDWARE AND SOFTWARE VERSIONS

In the apparatus of FIG. 3, an n stage shift register 195 is used in connection with a summing circuit 197 to successively count the number of clock pulses N accumulated from clock 126 during each step-time interval over a time period equal to n step-pulses or one pump cycle. In the embodiment of FIGS. 3 and 4, n=4 for simplicity in description. Preferably, n=2560 and the step-pulse signal averages at 100Hz (100 pulses/sec); the reference clock is at 1 MHz ($10^6$/pulses/sec) so that typical values of step-time are 10,000 counts.

Clock pulses from clock 126 are coupled to the CLK input terminal of counter 189, while the step-pulse signal from divider 166 is coupled to the "re-set" terminal of counter 189 and the "shift" terminal of register 195. Thus, each step-pulse causes the count in counter 189 for the latest step to be shifted into the first stage ($t_1$) of register 195, and all other locations to be left-shifted by one, and counter 189 to be re-set; while the contents of stages $t_1$ through $t_4$ are summed in summer 197 to produce N the sum of the clock count of the n-most recent shift register entries. This process is shown in graphic form in FIG. 4, which is an amplitude versus time plot of eight successive step motor pulses. The brackets identify four complete cycle time intervals $N_1-N_4$ being measured. Note the subscript 1 denotes the most recent time interval or cycle time measurement, the subscript 2, the next most recent measurement, etc.

The integers below each time variable $t_1$, $t_2$, etc. indicate the step-time counts associated with each interval. These numbers are chosen for the purposes of illustration, only, and do not represent actual operating conditions. The four most recent step-time counts are stored in registers 1 through 4, as shown in FIG. 3.

In the illustration of FIG. 4, the cycle time $N_4$ is given by $N_4 = t_6 + t_5 + t_4 = 10 + 21 + 15 + 12 = 58$. For $N_3$, the cycle time is given by $N_3 = t_6 + t_5 + t_4 + t_3 = 21 + 15 + 12 + 10 = 58$. Note that $t_3$ has been shifted in, and $t_7$ has been shifted out. Similarly, $N_2 = t_5 + t_4 + t_3 + t_2 = 15 + 12 + 10 + 21 = 58$, and $N_1 = t_4 + t_3 + t_2 + t_1 = 12 + 10 + 21 + 15 = 58$. $N_1$ is the most recent cycle time.

Note that in these examples, although the step-times within each interval are not constant (due to motor speed modulations), the overall cycle times $N_1$, $N_2$, $N_3$, $N_4$, etc., remain constant. Thus, the pump produces constant volumetric flow. Noise and changing load conditions could result in temporary deviation of N from the constant number N, in which case, F will no longer equal F-SET and the error signal ΔF will be adjusted accordingly to modify P-SET, which in turn adjusts the output of VCO 165 to speed up or slow down the output pulses from the VCC, as appropriate (See FIG. 2).

A more numerically efficient approach to calculating each N is to subtract the count exiting the shift register and add the count entering the shift register from the sum of the counts in the register, as follows:

$$N_3 = N_4 - t_7 + t_3 = 58 - 10 + 10 = 58$$

$$N_2 = N_3 - t_6 + t_2 = 58 - 21 + 21 = 58$$

$$N_1 = N_2 - t_5 + t_1 = 58 - 15 + 15 = 58$$

The above shows that the alternate method is equivalent. This method can be implemented in software, as shown in the flow chart of FIG. 5. The clock pulse count of the n-most recent clock pulse intervals is stored in n-RAM locations. In STEP 1, the address of the "current" memory location is set to 1 and the contents of all locations are set to 0. When the next motor step-pulse occurs (STEP 2), the numerical count in the current location is subtracted from the total count N (STEP 3).

In STEP 4, the step-time counter value accumulated while waiting for the aforesaid step (typically 10,000) is read and the value stored in the current location. The value is also added to N to update N. In STEP 5, the counter is re-set. Next, the current memory location is set to the next position in memory to be ready for the next step signal.

In the embodiment of FIG. 2, the number of clock pulses N during each step-time interval over n step-pulses (equal to one pump cycle) is calculated. Another alternative would be to compute the time per step-pulse in circuit 191 using the clock pulses 126 as a time measure precisely as described above. The time per step-pulse is then outputted from circuit 191 and inverted in inverter 193 to produce the step-pulse frequency which is now compared with a reference frequency F-SET corresponding to the desired step-pulse frequency, rather than the desired cycle frequency. In all other respects, the circuit would operate as shown in FIG. 2.

V. SPEED/FREQUENCY CORRECTION EMBODIMENT

Figure 6:
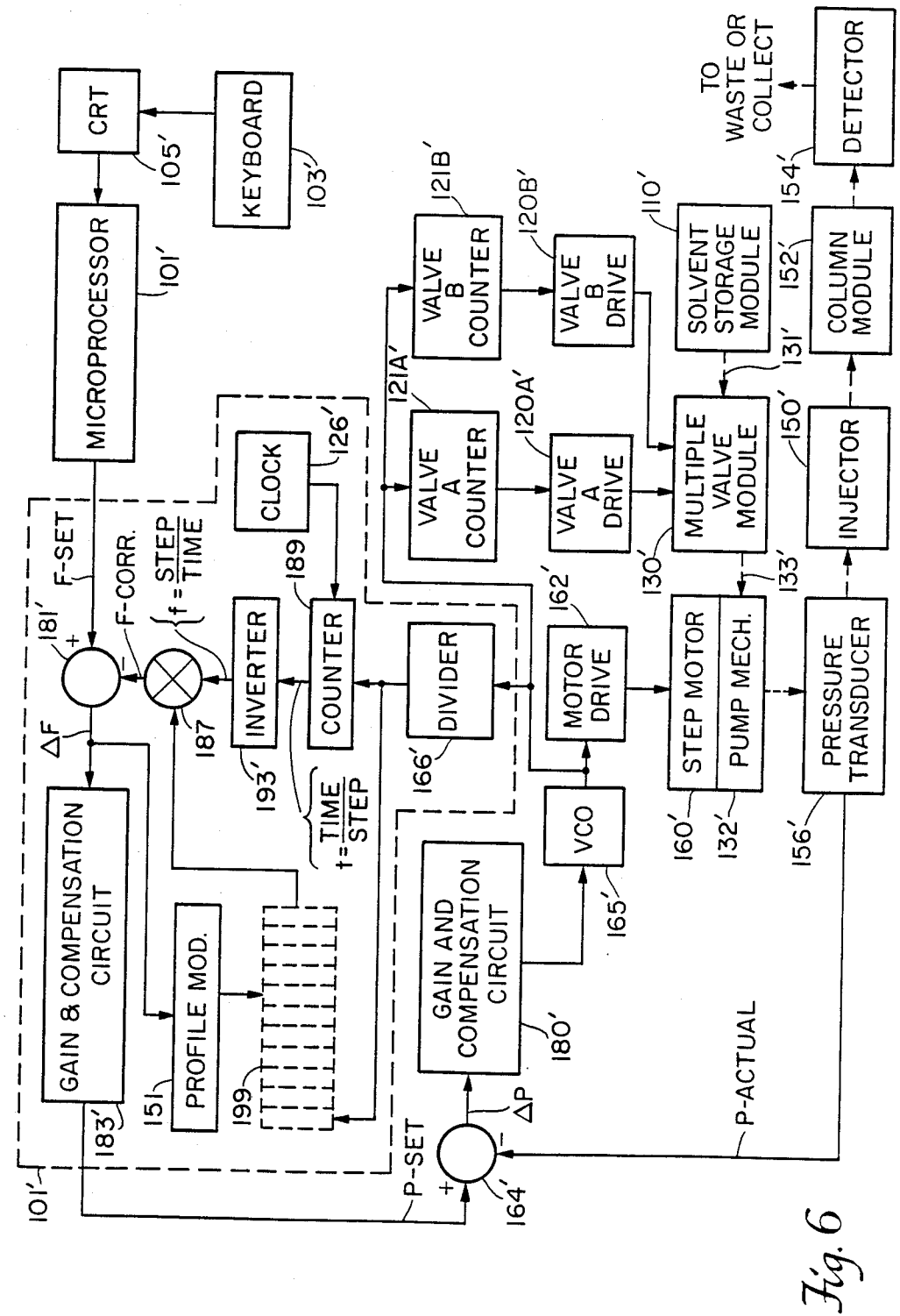
FIG. 6 is a block diagram of an alternate embodiment of the invention in which the outer loop utilizes a frequency correcting profile.
Figure 7:
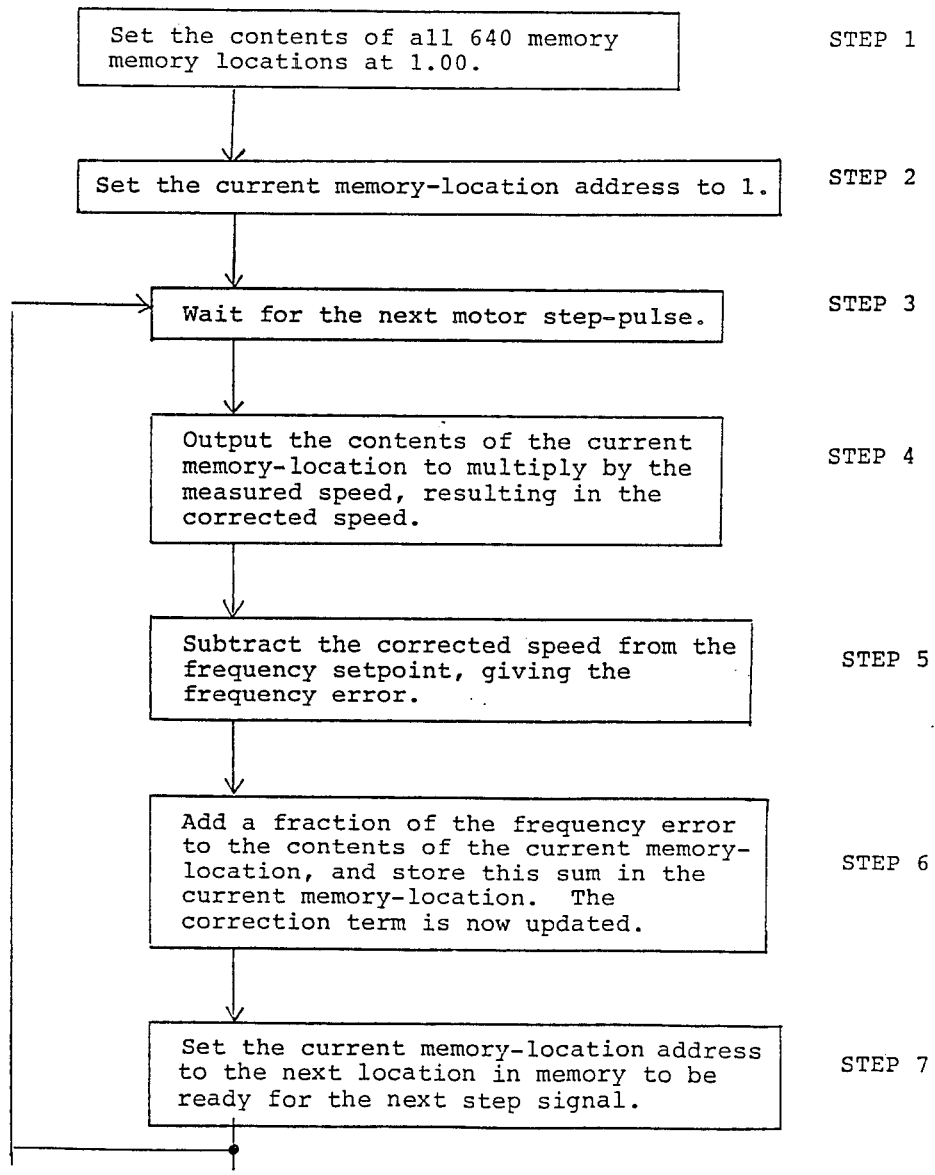
FIG. 7 is a flow chart of the software steps for implementing the frequency correcting profile circuit of FIG. 6.

In this embodiment, the outer loop utilizes a sequence of numbers stored in a circular memory to produce a speed/frequency correction-profile to continuously correct measured motor speed such that the corrected speed will be proportional to the volumetric flow irrespective of cyclical speed modulations introduced by the inner loop. The circular memory, as shown in FIG. 6, has "n" locations; wherein "n" is an integral multiple or submultiple of the number of motor-pulses required to produce one pump cycle. In a specific embodiment, n=2560 motor pulses/cycle divided by 4=640 step-pulses per cycle. This embodiment will now be described in detail in connection with FIGS. 6 and 7, wherein items previously described in connection with FIG. 2 carry like numerals with a prime suffix. These like items will not generally be discussed further, except to note that the entire inner loop is unchanged.

In the embodiment of FIG. 6, the circular memory is designated 199 and has 640 locations numbered 1 through 640. The memory is circular in that location 1 follows location 640.

The sequence of numbers in memory will be referred to as the "correction-profile". The memory 199 stores a speed correction term, i.e., the correction-profile, for each of 640 positions, i.e., one correction term for each step-pulse, throughout the pump cycle. The correction sequence is shown in the flow chart of FIG. 7. In STEP 1, all 640 locations are set to ONE. The current memory position is set to number ONE. In STEP 2, the clock pulses from clock 126' are accumulated in counter 189 until the next motor step-pulse occurs (STEP 3). The speed correction term in the current memory location for the current pump position is outputted and multiplied in multiplier 187 by the measured speed "f"=step/time to produce corrected speed (F-CORR) (See STEP 4). Speed "f" is produced by inverting the count (t =time/step) in counter 189. To the extent that the correction-profile is correct, the corrected speed will be proportional to the true flow being pumped, irrespective of the speed modulations which occur on a cyclical basis as a natural result of using the inner pressure loop.

The above correction process is shown graphically in FIGS. 8A–8B wherein FIG. 8A is a plot of a typical amplitude versus time measured speed signal "f" for one cycle from which it can be seen that large speed variations occur on a cyclical basis. These large perturbations are largely eliminated, as shown in FIG. 8C, by multiplying the measured speed with the stored correction-profile signal, FIG. 8b.

In STEP 5, the corrected frequency F-CORR is subtracted in summing junction 181' from the frequency setpoint F-SET to arrive at a frequency error $\Delta F$. To the extent that there is a frequency error, the gain and compensation circuit 183' adjusts the pressure setpoint P-SET in order to correct this error. If the frequency error $\Delta F$ is positive, the pressure setpoint is adjusted upwards, and vice versa, if the frequency error is negative.

If the frequency error at a given position persists over a number of cycles, then it is likely that the correction-profile value for that position is in error. Thus, the correction profile is updated on a longer term basis than the pressure setpoint. The manner in which the correction profile is updated is outlined below:

At a given position in the pump cycle, the speed correction term for that position, corresponding to one particular memory location, is being multiplied by the actual measured speed to yield the corrected speed. An error between the corrected speed and the speed setpoint is sensed by profile-modifier 151. The speed correction term in that memory location is then updated by adding a fraction of the error to it (STEP 6). Thus, one cycle (640 steps) later, this updated value is used as the correction term for that motor position. The fraction is chosen appropriately so that it will require multiple cycles for the correction-profile to be fully updated. This assures that it will not be sensitive to random disturbances.

The process described in the above paragraph is repeated, using successive correction-profile memory locations, each time a motor step-pulse is received. In this specific example, that is 640 times per pump cycle. Thus, succeeding locations in memory are updated every step signal, but an individual memory location is updated only once per pump cycle, at the time when the motor is in the position which corresponds to that individual memory location.

After the updating process has been allowed to run over several cycles, the correction-profile becomes essentially correct, and the corrected speed a true representation of flow being produced by the pump. This greatly reduces pressure and flow ripples caused by the motor's cyclical speed modulations, which are cancelled by the correction profile term.

VI. FLOW REFERENCE LEVEL EMBODIMENT

In the alternate embodiment shown in FIG. 9, a flow reference level signal set by the user via the microprocessor 101 is multiplied in multiplier 904 by a correction term from correction profile 199' to produce a corrected speed signal which controls the frequency of VCO 165. This corrected speed signal drives VCO 165 to set the motor speed of motor 160 and thus the pump flow from pump mechanics 132.

The correction terms are stored in correction profile 199' in a RAM memory containing n locations, one for each step-pulse in a pump cycle. The step-pulses are numbered uniquely from #1 through #n, corresponding to locations #1 through #n in memory. The step-pulses are generated by a divider 166, as in previous embodiments. At each successive step-pulse, the correction profile term is indexed to the next location in memory, to correct the speed in that section of the pump cycle. As before, the memory is circular in that location #1 is considered to follow location #n.

The profile term stored in correction profile 199' corresponding to the current step-pulse number is modified by the profile modifier 151' based on the pressure error $\Delta P$ from summing point 902. A fraction of the error $\Delta P$ is added to the current correction term to form the corresponding correction term for the next cycle. This modification is applied once each step-pulse to the current correction term. Thus, succeeding locations in memory are updated every step signal, but an individual memory location is updated only once per pump cycle, at the time when the pump is in the position which corresponds to that individual memory location. In this manner, the correction profile is updated to adjust for changing pump operating conditions.

The signal $\Delta P$ is formed by subtracting the actual pressure P-ACTUAL from a pressure estimate signal P-EST at summing point 902. Pressure estimator or predictor 900 forms an estimate of the expected value of the current pressure, based on past measurements of the pressure from tranducer 156. The estimator may be formed by low-pass filtering the actual pressure signal.

Alternately, a well-known Kalman filter may be used to produce a least mean-square error estimate of the expected pressure based on the actual pressure signal. For a general treatment of estimators, or predictors, see Astrom and Wittenmark Computer Control System © 1984, Prentice Hall.

In other respects, the system of FIG. 9 is similar to the system of FIG. 6. The key advantage is the absence of any direct pressure or flow feedback loop. The only loop required is the profile modifier loop, which uses measured pressure to drive its modifications.

VII. General

In the embodiments utilizing the clock pulses, the measured frequency parameter F is directly related to the actual/delivered volumetric flow by virtue of constant conversion factor related to the swept volume of the pump. The user, therefore, has available the option to either control volumetric flow by an open-loop mode using divided clock pulses from the clock coupled in place of VCO pulses or a closed-loop mode in which the VCO and associated sensing and feedback circuitry are utilized, as illustrated. Since either of the rates are well matched, it is straightforward to revert from one to the other, as conditions dictate. For example, during a sample injection sequence, when hydraulic resistance is erratic, the system can be momentarily run in an open-loop, constant step rate mode. Once injection is accomplished, the system may be reverted to closed loop mode for optimizing sample detection and quantitation.

At initial start-up from zero pressure, the user may enable open loop mode for several strokes in order to sample the back pressure and facilitate rapid convergence on the correct pressure reference level for inner loop operation. The system produces extremely smooth and accurate compositional delivery together with nearly complete elimination of pulsile variations in volumetric delivery. These properties are required in order to interface successfully with many new and highly sensitive LC detectors.

EQUIVALENTS

Although preferred embodiments have been set forth in detail above, this is solely for the purpose of illustration. As such, numerous modifications may become apparent to those of skill in the art. Generation and maintenance of accurate volumetric flow and mixing of a plurality of liquids has been shown as functioning in a gradient mode of chromatographic operation, but the principles illustrated can be adapted to perform on-line mixed isocratic operation, or single-solvent isocratic operation, in which case, proportioning valves are not required, or to perform flow rate programming, i.e., varying over time the mixture flow rate instead of its composition to achieve the desired chromatographic separations. The various implementations of the invention may be in analog or digital form and may further be embodied in hardware or software.

While step motors have been suggested for implementing the invention, any conventional motor, such as a D.C. motor, may be substituted, along with well-known encoding mechanisms, to produce the requisite step-pulses for timing purposes.

Furthermore, while a two piston pump has been chosen for the preferred embodiment, single or multiple cylinder pumps may be readily adapted for use, in accordance with the principles of the invention. Therefore, the invention is to be construed in light of the foregoing and the appended claims.

We claim:
1. A pumping system for flow control which includes a motor driven pump for pumping fluid by pistons to a load comprising:
(a) control means for compensating for cyclical variations in the relation between the speed of the motor and volumetric flow of the pump to maintain essentially constant volumetric flow from the pump, said control means including means for adjusting to changing pump operating conditions throughout the course of pump operation independent of pump piston position by generating a flow signal proportional to the instantaneous volumetric flow of the pump and using the flow signal to vary a pressure reference signal which in turn controls the motor speed; said changing operating conditions resulting in modifications to the character of said cyclical variations.

2. The system of claim 1 wherein the control means comprises:
(a) an inner feedback loop having:
   (i) a pressure reference level signal;
   (ii) speed adjusting means responsive to sensed fluid pressure from the load for adjusting the speed of the motor, in accordance with the difference between said sensed pressure and said pressure reference level signal, to reduce said difference; and
(b) an outer feedback loop having:
   (i) a flow reference level signal;
   (ii) measuring means for measuring the speed of the motor to produce a speed signal, and for converting said speed signal into a flow signal proportional to actual instantaneous volumetric flow from the pump;
   (iii) pressure control means responsive to said flow signal for adjusting said pressure reference level signal, in accordance with the difference between said flow signal and said flow reference level signal, to reduce said difference to maintain substantially constant fluid flow from said pump at the flow reference level.

3. The system of claim 2 wherein the measuring means includes pulse generator means for generating n step-pulses which occur during each cycle of the pump, and wherein the measured motor speed is averaged over the interval encompassing the n-most recently occurring step-pulses to produce said speed signal, such that said speed signal represents the average speed for the most recent n step-pulses, which comprises the most recent cycle of pump operation and wherein, said speed signal is converted to an actual flow signal which is proportional to true pump flow, independent of the cyclic speed variations of the pump.

4. A pumping system for flow control which includes a motor driven pump for pumping fluid to a load comprising:
(a) control means for compensating for cyclical variations in the relation between the speed of the motor and volumetric flow of the pump to maintain essentially constant volumetric flow from the pump, said control means including means for adjusting to changing pump operating conditions throughout the course of pump operation; said changing operating conditions resulting in modifications to the character of said cyclical variations; said control means comprising:
an inner feedback loop having:
   (i) a pressure reference level signal;
   (ii) speed adjusting means responsive to sensed fluid pressure from the load for adjusting the speed of the motor, in accordance with the difference between said sensed pressure and said pressure reference level signal, to reduce said difference; and
an outer feedback loop having:
   (i) a flow reference level signal;
   (ii) measuring means for measuring the speed of the motor to produce a speed signal, and means for converting said speed signal into a flow signal proportional to actual instantaneous volumetric flow from the pump; and wherein the measuring means comprises a pulse generator for generatthe rate of said step-pulses and wherein n-step pulses correspond to one complete pump cycle;

(iii) a pressure reference level signal;

(iv) control means responsive to fluid pressure sensed from the load for adjusting the rate of said step-pulses in accordance with the difference between said sensed pressure and said pressure reference level signal;

(b) an outer feedback loop comprising:

(i) calculator means for successively determining the total time duration of the n-most recent pulses, or multiples, or submultiples thereof, to produce a timing signal corresponding to the time it took to complete the most recent pump cycle or multiple or submultiple thereof; and (ii) control means responsive to said timing signal for adjusting said pressure level signal to maintain substantially constant volumetric fluid flow from said pump by successively comparing said timing signal with a timing reference signal and adjusting the pressure reference level signal in accordance with the difference between the timing signal and the timing reference signal; and wehrein the calculator means includes:

(a) a clock pulse generator for generating a series of timing pulses; and (b) a counter responsive to said step-pulses or multiples, or submultiples thereof, for counting the number of timing pulses generated from one step-pulse or multiple, or submultiple thereof, to the next; and (c) a shift register having n stages or multiples, or submultiples thereof, for successively and separately accepting the count of the timing pulses from the generator for each n-most recent step-pulses, or multiples, or submultiples thereof, to produce successive step-times in successive stages of said register; and (d) summing means for adding the count of the timing pulses generated between the two most recent step-pulses, or multiple, or submultiples thereof, to the count of the total of the n-most recent step-pulses, or multiples, or submultiples, thereof, and subtracting from the count the value of the least recently measured step-time in the n-stage shift register.

27. In a fluid delivery system, the combination comprising:

(a) an inner feedback loop having:

(i) pulse generator means for generating step-pulses;

(ii) a fluid dispensing pump for delivering fluid to a load, said pump being controlled by a motor, and wherein the speed of the motor is proportional to the rate of said step-pulses and wherein n-step pulses correspond to one complete pump cycle;

(iii) a pressure reference level signal;

(iv) control means responsive to fluid pressure sensed from the load for adjusting the rate of said step-pulses in accordance with the difference between said sensed pressure and said pressure reference level signal;

(b) an outer feedback loop comprising:

(i) calculator means for successively determining the total time duration of the n-most recent pulses, or multiples, or submultiples thereof, to produce a timing signal corresponding to the time it took to complete the most recent pump cycle or multiple or submultiple thereof and wherein said calculator means further includes:

(a) a memory device having n storage locations wherein n is a multiple, or submultiple of the number of motor steps per pump cycle; and into which is stored a speed/frequency correction factor for each of the n current motor positions; and (b) means for inverting the timing signal to produce a frequency signal;

(c) multiplier means for successively multiplying the inverted timing signal by said factor to correct said frequency signal for cyclical speed variations; and (ii) control means responsive to said timing signal for adjusting said pressure level signal to maintain substantially constant volumetric fluid flow from said pump by successively comparing said timing signal with a timing reference signal and adjsuting the pressure reference level signal in accordance with the difference between the timing signal and the timing reference signal.

* * * * * pressure reference level signal, to reduce said difference; and an outer feedback loop having:
(i) a flow reference level signal;
(ii) measuring means for measuring the speed of the motor to produce a speed signal, and means for converting said speed signal into a flow signal proportional to actual instantaneous volumetric flow from the pump independent of the cyclic speed variations of the pump; and wherein the measuring means includes pulse generator means for generating n step-pulses which occur during each cycle of the pump, and wherein the measured motor speed is averaged over the interval encompassing the n-most recently occurring step-pulses to produce said speed signal, such that said speed signal represents the average speed for the most recent n step-pulses, which comprises the most recent cycle of pump operation; and
(iii) pressure control means responsive to said flow signal for adjusting said pressure reference level signal, in accordance with the difference between said flow signal and said flow reference level signal, to reduce said difference to maintain substantially constant fluid flow from said pump at the flow reference level.

24. A pumping system for flow control which includes a motor driven pump for pumping fluid to a load comprising:
(a) control means for compensating for cyclical variations in the relation between the speed of the motor and volumetric flow of the pump to maintain essentially constant volumetric flow from the pump, said control means including means for adjusting to changing pump operating conditions throughout the course of pump operation; said changing operating conditions resulting in modifications to the character of said cyclical variations; said control means comprising:
an inner feedback loop having:
(i) a pressure reference level signal;
(ii) speed adjusting means responsive to sensed fluid pressure from the load for adjusting the speed of the motor, in accordance with the difference between said sensed pressure and said pressure reference level signal, to reduce said difference; and
an outer feedback loop having:
(i) a flow reference level signal;
(ii) measuring means for measuring the speed of the motor to produce a speed signal, and means for converting said speed signal into a flow signal proportional to actual instantaneous volumetric flow from the pump; and wherein the measuring means comprises:
(a) a clock pulse generator for generating a series of timing pulses; and
(b) a counter responsive to said step-pulse or multiples, or submultiples thereof, for counting the number of clock pulses generated from one step-pulse or multiples, or submultiples thereof, to the next;
(c) a shift register having n stages or multiples, or submultiples thereof, for successively separately accepting the count of the clock pulses from the counter for each n-most recent step-pulses or multiples or submultiples thereof, in successive stages of said register; and
(d) calculator means for computing the sum of the entries in each of the n stages of the shift register, and for inverting said sum to give said average speed signal; and
(iii) pressure control means responsive to said flow signal for adjusting said pressure reference level signal, in accordance with the difference between said flow signal and said flow reference level signal, to reduce said difference to maintain substantially constant fluid flow from said pump at the flow reference level.

25. In a fluid delivery system, the combination comprising:
(a) an inner feedback loop having:
(i) pulse generator means for generating step-pulses;
(ii) a fluid dispensing pump for delivering fluid to a load, said pump being controlled by a motor, and wherein the speed of the motor is proportional to the rate of said step-pulses and wherein n-step pulses correspond to one complete pump cycle;
(iii) a pressure reference level signal;
(iv) control means responsive to fluid pressure sensed from the load for adjusting the rate of said step-pulses in accordance with the difference between said sensed pressure and said pressure reference level signal;
(b) an outer feedback loop comprising:
(i) calculator means for successively determining the total time duration of the n-most recent pulses, or multiples, or submultiples thereof, to produce a timing signal corresponding to the time it took to complete the most recent pump cycle or multiple or submultiple thereof; and
(ii) control means responsive to said timing signal for adjusting said pressure level signal to maintain substantially constant volumetric fluid flow from said pump by successively comparing said timing signal with a timing reference signal and adjusting the pressure reference level signal in accordance with the difference between the timing signal and the timing reference signal; and wherein the calculator means includes:
(a) a clock pulse generator for generating a series of timing pulses; and
(b) a counter responsive to said step-pulse or multiples, or submultiples thereof, for counting the number of timing pulses generated from one step-pulse or multiple, or submultiple thereof, to the next; and
(c) a shift register having n stages or multiples, or submultiples thereof, for successively separately accepting the count of the timing pulses from the generator for each n-most recent step-pulses, or multiples, or submultiples thereof, in successive stages of said register; and
(d) summing means for successively summing the count in each register stage to generate said timing signal.

26. In a fluid delivery system, the combination comprising:
(a) an inner feedback loop having:
(i) pulse generator means for generating step-pulses;
(ii) a fluid dispensing pump for delivering fluid to a load, said pump being controlled by a motor, and wherein the speed of the motor is proportional to plete the most recent pump cycle or multiple or submultiple thereof; and (d) adjusting said pressure level signal to maintain substantially constant volumetric fluid flow from said pump by successively comparing said timing signal with a timing reference signal and adjusting the pressure reference level signal in accordance with the difference between the timing signal and the timing reference signal.

14. The method of claim 13 wherein the load is a liquid chromatography column and the pump is coupled by valves to a source of liquid solvents for delivery of said solvents to said column.

15. The method of claim 13 wherein the total time duration of the n-most recent pulses is determined by:
(a) generating a series of timing pulses; and
(b) counting the number of timing pulses generated from one step-pulse or multiple, or submultiple thereof, to the next.

16. The method of claim 15 wherein the counting is achieved by successively separately accepting the count of the timing pulses for each n-most recent step-pulses, or multiples, or submultiples thereof and successively summing the count to generate said timing signal.

17. The method of claim 15 wherein the counting is achieved by successively and separately accepting the count of the timing pulses for each n-most recent step-pulses, or multiples, or submultiples thereof to produce successive step-times adding the count of the timing pulses generated between the most recent step-pulses, or multiple, or submultiple thereof, to the count of the total of the n-most recent pulses, or multiples, or submultiples, thereof, and subtracting from the count the value of the least recently measured step-time.

18. A method by which a fluid is delivered to a load by a cyclical pump from valves coupled to a fluid source, and wherein the pump is driven by a motor the speed of which is a function of the number of motor pulses generated per unit time, and wherein the number of step-pulses generated per unit time is a multiple or submultiple of the number of motor pulses generated per unit time and the number of step-pulses required for one complete pump cycle is a known number n, comprising the steps of:
(a) sampling the back pressure of said load and generating a pressure signal proportional thereto;
(b) generating a pressure level reference signal proportional to a desired pressure level;
(c) comparing the pressure signal with the pressure level reference signal and generating a pressure error signal proportional to the difference between the two said signals;
(d) increasing or decreasing the speed of said pump, in accordance with the sense and magnitude of said error signal;
(e) calculating the time N it takes to complete one motor revolution during each of the n-most recent step-pulses, or an integral multiple or submultiple thereof, and correcting the pressure level reference signal to the extent the time N results in a deviation of measured motor speed from desired motor speed.

19. A pumping system for flow control which includes a motor driven pump for pumping fluid to a load comprising:
(a) control means for compensating for cyclical variations in the relation between the speed of the motor and volumetric flow of the pump to maintain essentially constant volumetric flow from the pump, said control means including means for adjusting to changing pump operating conditions throughout the course of pump operation; said changing operating conditions resulting in modifications to the character of said cyclical variations; and wherein the control means comprises:
(b) pulse generator means for generating n step-pulses which occur during each cycle of the pump;
(c) flow reference generator means for generating a flow reference level signal proportional to a desired fluid flow level;
(d) pressure sensor means for sensing fluid pressure at the load and generating a sensed pressure signal proportional thereto;
(e) pressure reference generator means for generating a pressure reference level signal at the occurrence of each step-pulse, said pressure reference level siqnal being proportional to the expected pressure level at each current step-pulse;
(f) correction profile means for storing correction term signals for each corresponding step-pulse;
(g) correction means responsive to the difference $\Delta P$ between said pressure reference level signal and said sensed pressure signal for adjusting at each step-pulse during each cycle of pump operation, said correction term signal in accordance with said difference $\Delta P$;
(h) multiplier means for multiplying said flow reference level signal at each step-pulse by said correction term signal corresponding to said step-pulse to provide a corrected motor speed signal;
(i) motor speed adjusting means for adjusting the speed of said motor, in accordance with said corrected motor speed signal, to cancel cyclical variations in the relation between motor speed and pump flow, such that fluid flow out of the pump is substantially constant.

20. The system of claim 19 wherein the pressure reference generator means comprises an estimator coupled to the pressure sensor means; which estimator, in response to said sensed pressure signal, generates an estimate of the expected pressure value at each step-pulse.

21. The system of claim 19 wherein at each step-pulse, a fraction of the difference $\Delta P$ is added to the correction term signal by the correction means.

22. The system of claim 19 wherein the corresponding correction term signal is adjusted to reduce the difference $\Delta P$ to maintain said correction term at a level which produces substantially constant fluid flow from the pump at the level of the reference level signal.

23. A pumping system for flow control which includes a motor driven pump for pumping fluid to a load comprising:
(a) control means for compensating for cyclical variations in the relation between the speed of the motor and volumetric flow of the pump to maintain essentially constant volumetric flow from the pump, said control means including means for adjusting to changing pump operating conditions throughout the course of pump operation; said changing operating conditions resulting in modifications to the character of said cyclical variations; said control means comprising:
an inner feedback loop having:
(i) a pressure reference level signal;
(ii) speed adjusting means responsive to sensed fluid pressure from the load for adjusting the speed of the motor, in accordance with the difference between said sensed pressure and said ing n step-pulses which occur during each cycle of the pump, and multiplying means for multiplying the measured motor speed at each such step-pulse by a correction term corresponding to the then current step-pulse number, to yield a corrected speed signal; said corrected speed signal comprising said flow signal proportional to true pump flow, independent of the pump cyclic speed variations; and correction means responsive to said flow signal for adjusting, at each step-pulse during each cyclic of pump operation, said corresponding correction term, in accordance with the difference between said flow signal and said flow reference level signal, to reduce said difference to maintain said correction term at a level which will produce substantially constant fluid flow from said pump at the level of the flow reference level signal;
  (iii) pressure control means responsive to said flow signal for adjusting said pressure reference level signal, in accordance with the difference between said flow signal and said flow reference level signal, to reduce said difference to maintain substantially constant fluid flow from said pump at the flow reference level.

5. The system of claim 4 wherein said correction means is stored in a memory having n locations.

6. In a fluid delivery system, the combination comprising:
(a) an inner feedback loop having:
  (i) pulse generator means for generating step-pulses;
  (ii) a fluid dispensing pump for delivering fluid to a load, said pump being controlled by a motor, and wherein the speed of the motor is proportional to the rate of said step-pulses and wherein n-step pulses correspond to one complete pump cycle;
  (iii) a pressure reference level signal;
  (iv) control means responsive to fluid pressure sensed from the load for adjusting the rate of said step-pulses in accordance with the difference between said sensed pressure and said pressure reference level signal;
(b) an outer feedback loop comprising:
  (i) calculator means for successively determining the total time duration cf the n-most recent pulses, or multiples, or submultiples thereof, to produce a timing signal corresponding to the time it took to complete the most recent pump cycle or multiple or submultiple thereof; and
  (ii) control means responsive to said timing signal for adjusting said pressure level signal to maintain substantially constant volumetric fluid flow from said pump by successively comparing said timing signal with a timing reference signal and adjusting the pressure reference level signal in accordance with the difference between the timing signal and the timing reference signal.

7. The fluid delivery system of claim 6 wherein the load is a liquid chromatography column and the pump is coupled by valves to a source of liquid solvents for delivery of said solvents to said column.

8. A fluid system having a load to which a fluid is delivered by a cyclical pump from valves coupled to a fluid source, and wherein the pump is driven by a step motor the speed of which is a function of the number of motor pulses generated per unit time, and wherein the number n of step-pulses required for one complete pump cycle is a predetermined number, and the number of step-pulses per unit time is a multiple or submultiple of the number of motor pulses per unit time comprising:
(a) a pressure feedback loop having:
  (i) a pressure transducer coupled to said load for sampling the back pressure of said load and generating a pressure signal proportional thereto;
  (ii) a pressure level reference generator for generating a pressure level reference signal proportional to a desired pressure level;
  (iii) comparator means for comparing the pressure signal with the pressure level reference signal and generating a pressure error signal proportional to the difference between the two said signals;
  (iv) driver means responsive to said error signal for increasing or decreasing the speed of said pump, in accordance with the sense and magnitude of said error signal; and
(b) an outer feedback loop for calculating the time N it takes to complete one motor revolution during each of the n-most recent step-pulses, or an integral multiple or submultiple thereof, and correcting the pressure level reference signal to the extent the time N results in a deviation of motor speed from a reference speed.

9. The system of claim 8 wherein inverter means is included for inverting the time N to produce measured frequency F which is compared with referenced speed to produce an error signal for correcting the pressure level reference signal.

10. The system of claim 8 wherein the outer feedback loop comprises:
(a) a clock pulse generator for generating a series of accurate timing pulses;
(b) a counter for counting said pulses in increments corresponding to the step-pulses or integral multiples or submultiples thereof; and
(c) summing means for summing the n-most recent step-pulses or integral multiples or submultiples thereof.

11. The system of claim 8 including:
(a) memory device having n storage location wherein n is a multiple or submultiple of the number of motor steps per pump cycle and into which is stored a speed/frequence correction factor for each of the n current motor positions;
(b) inverter means for inverting the step-time to determine the corresponding step-frequency f; and
(c) multiplier means for successively multiplying the inverted time by said factor to correct said frequency.

12. The system of claim 8 wherein the load is a liquid chromatography column, and the fluid is a solvent metered by valves coupled to said pump, the driver means comprises a voltage variable controlled oscillator which produces step-pulses at a variable rate, in accordance with the magnitude and sense of said error signal.

13. A method of pumping fluid to a load comprising the steps of:
(a) delivering fluid from a motor controlled pump wherein the speed of the motor is proportional to the rate of a series of step-pulses such that n-such pulses correspond to one complete pump cycle;
(b) sensing fluid pressure from the load and adjusting the rate of said step-pulses in accordance with the difference between said sensed pressure and a pressure reference level signal;
(c) successively, for each step-pulse, determining the total time duration of the n-most recent step-pulse, or multiples, or submultiples thereof, to produce a timing signal corresponding to the time it took to com-

UNITED STATES PATENT AND TRADEMARK OFFICE
CERTIFICATE OF CORRECTION

PATENT NO. : 4,767,279
DATED : Aug. 30, 1988
INVENTOR(S) : Theodore A. Dourdeville and David L. Trumper It is certified that error appears in the above—identified patent and that said Letters Patent is hereby corrected as shown below:

Cover page, item [22], filing date should be June 2, 1987.

Column 21, line 60, "step-pulse" should be ---step-pulses---.

Column 17, line 11, "cyclic" should be ---cycle---.

Column 22, line 48, "step-pulse" should be ---step-pulses---.

Column 23, line 24, "wehrein" should be ---wherein---.

Signed and Sealed this

Twenty-seventh Day of June, 1989

Attest:

DONALD J. QUIGG

Attesting Officer

Commissioner of Patents and Trademarks